(12) United States Patent
LaCourse et al.

(10) Patent No.: US 7,923,259 B2
(45) Date of Patent: Apr. 12, 2011

(54) PLATFORM FOR ANALYSIS LIQUID SAMPLES

(75) Inventors: William R. LaCourse, Catonsville, MD (US); Ronita L. Marple, Ellicott City, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 0 days.

(21) Appl. No.: 12/320,649

(22) Filed: Jan. 30, 2009

(65) Prior Publication Data

US 2009/0200181 A1 Aug. 13, 2009

Related U.S. Application Data

(62) Division of application No. 10/849,293, filed on May 20, 2004, now abandoned.

(60) Provisional application No. 60/471,814, filed on May 20, 2003, provisional application No. 60/527,936, filed on Dec. 8, 2003.

(51) Int. Cl.
*G01N 30/02* (2006.01)
(52) U.S. Cl. ...................................... 436/161
(58) Field of Classification Search .................. 436/161
See application file for complete search history.

(56) References Cited

U.S. PATENT DOCUMENTS 5,462,660 A 10/1995 Singleton et al.

OTHER PUBLICATIONS

Patsias, J.; Papadopoulou-Mourkidou, E. "Development of an automated on-line solid phase extraction-high-performance liquid chromatographic method for the analysis of aniline, phenol, caffeine, and various selected substituted aniline and phenol compounds in aqueous matrices." Journal of Chromatography A, 2000, 904, pp. 171-188.*

Leggett, D.C.; Jenkins, T. F.; Miyares, P. H. "Salting-out Solvent Extraction for Preconcentration of Neutral Polar Organic Solutes from Water." Analytical Chemistry, 1990, 62, pp. 1355-1356.*

Puig, D.; Barcelo, D. "Comparative study of on-line solid phase extraction followed by UV and eletrochemical detection in liquid chromatography for the determination of priority phenols in river water samples." Analytica Chimica Acta, 1995, 111, pp. 63-69.*

Bratin, K., et al., "Recent advances in LCEC and voltammetry. A Report on the Fourth International Symposium," *Am. Lab.* 16:33, 36, 40, 45, 46, 48, 52-56, 59, 61, 62, International Scientific Communications (1984).

Jenkins, T.F., and Grant, C.L., "Comparison of Extraction Techniques for Munitions Residues in Soil," *Anal. Chem.* 59:1326-1331, American Chemical Society (1987).

(Continued)

*Primary Examiner* — Walter D Griffin
*Assistant Examiner* — Bobby Ramdhanie
(74) *Attorney, Agent, or Firm* — Sterne, Kessler, Goldstein & Fox P.L.L.C.

(57) ABSTRACT

The present application relates to apparatus for sampling and analysis of analytes in a liquid sample. A liquid sample is pre-concentrated using a chromatographic column prior to analysis via a two stage analysis apparatus. A high-performance liquid chromatography system with ultra violet detection may be used in conjunction with electrochemical detection for the analysis of environmental contaminants, including explosive residues. The present invention also provides for on-site analysis of such contaminants. The present invention also provides for methods of analyzing the components of a liquid sample, including methods for on-site analysis.

18 Claims, 8 Drawing Sheets

OTHER PUBLICATIONS

Figure 1:
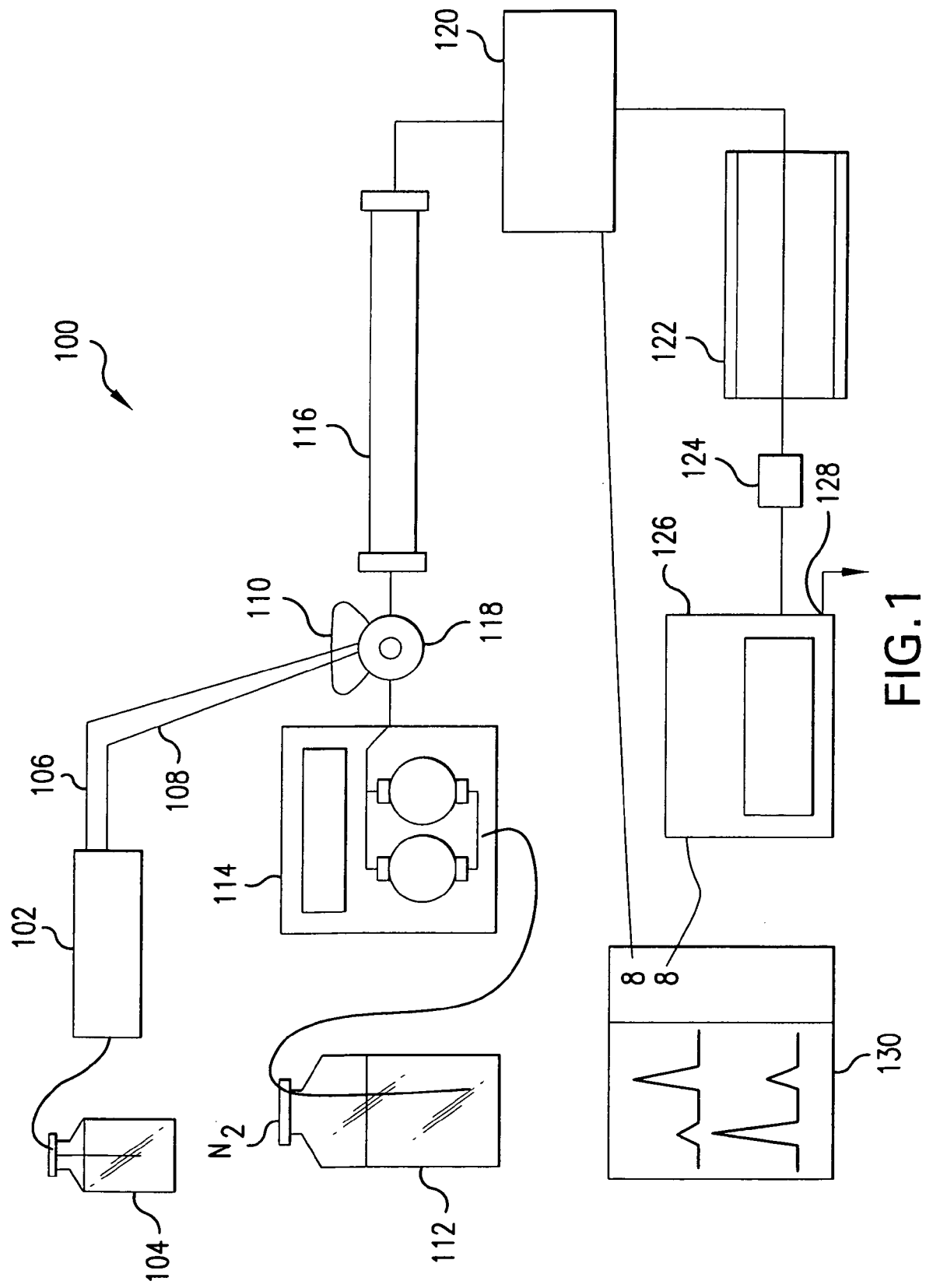

Koenigbauer, M.J., and Majors, R.E., "Sample Cleanup in High Performance Liquid Chromatography Using On-Line Multidimensional Techniques," *LC GC* 8:510, 512-514, Aster Pub. Corp. (1990).

Krstulović, A.M., and Brown, P.R., *Reversed-Phase High-Performance Liquid Chromatography. Theory, Practice, and Biomedical Applications*, John Wiley & Sons, New York, NY, pp. 1-31 (1982).

Krull, I.S., and LaCourse, W.R., "Post-Column Photochemical Derivatizations for Improved Detection and Identification in HPLC," in *Reaction Detection in Liquid Chromatography*, Krull, I.S., ed., Marcel Dekker, Inc., New York, NY, pp. 303-352 (1986).

Krull, I.S., et al., "Electrochemical detection in HPLC," *LC GC* 2:214-219, 221, Aster Pub. Corp. (1984).

Krull, I.S., et al., "LCEC for trace analysis. Recent Advances in Instrumentation, Methods, and Applications," *Am. Lab.* 15:57-60, 62-65, International Scientific Communications (1983).

Krull, I.S., et al., "Oxidative LCEC of Organic Nitro Compounds," *Curr. Sep.* 5:57-62, Bioanalytical Systems (1984).

Krull, I.S., et al., "Photochemical derivatizations for improved detection in high performance liquid chromatography," *LC GC* 7:758-760, 762, 764, 766-769, Aster Pub. Corp. (1989).

Krull, I.S., et al., "The Trace Analysis for Explosives and Related Compounds Via Liquid Chromatography-Electrochemistry (LCEC)," in *Proceedings of the International Symposium on the Analysis and Detection of Explosives*, FBI, U.S. Government Printing Office, Washington, DC, pp. 11-29 (1983).

Martens, D.A., and Frankenberger Jr., W.T., "Determination of Glycuronic Acids by High-Performance Anion Chromatography With Pulsed Amperometric Detection," *Chromatographia* 30:651-656, Vieweg Und Sohn Verlags Gmbh (1990).

Ramsteiner, K.A., "Systematic Approach to Column Switching," *J. Chromatogr.* 456:3-20, Elsevier (1988).

Richter, B.E., et al., "Accelerated Solvent Extraction: A Technique for Sample Preparation," *Anal. Chem.* 68:1033-1039, American Chemical Society (1996).

Selavka, C.M., and Krull, I.S., "Liquid Chromatography with Photolysis-Electrochemical Detection for Nitro-Based High Explosives and Water Gel Formulation Sensitizers," *J. Energetic Materials* 4:273-303, Dowden, Brodman & Devine, Inc. (1986).

Yinon, J., and Zitrin, S., *Modern Methods and Applications in Analysis of Explosives*, John Wiley & Sons, New York, NY, p. 51 (1993).

Yinon, J., *Toxicity and Metabolism of Explosives*, CRC Press, Boca Raton, FL, Preface and p. 75 (1990).

Dasenbrock, C.O., and, LaCourse, W.R., "Assay for cephapirin and ampicillin in raw milk by high-performance liquid chromatography—integrated pulsed amperometric detection," *Anal. Chem.* 70:2415-2420, American Chemical Society (1998).

Liu, H., et al., "Optimization of post-column photolysis and electrochemical detection for the liquid chromatographic determination of 3-nitro-L-tyrosine," *J Chromatogr. A.* 818:69-75, Elsevier (1998).

Mattusch, J., et al., "HPLC/UV-spectrometric and electrochemical detection of lignin-decomposition products in alcoholic beverages," *Fresenius J. Anal. Chem.* 340:426-430, Springer International (1991).

Non-Final Office Action for U.S. Appl. No. 10/849,293, filed on May 20, 2004, mailed on Jul. 31, 2008.

* cited by examiner

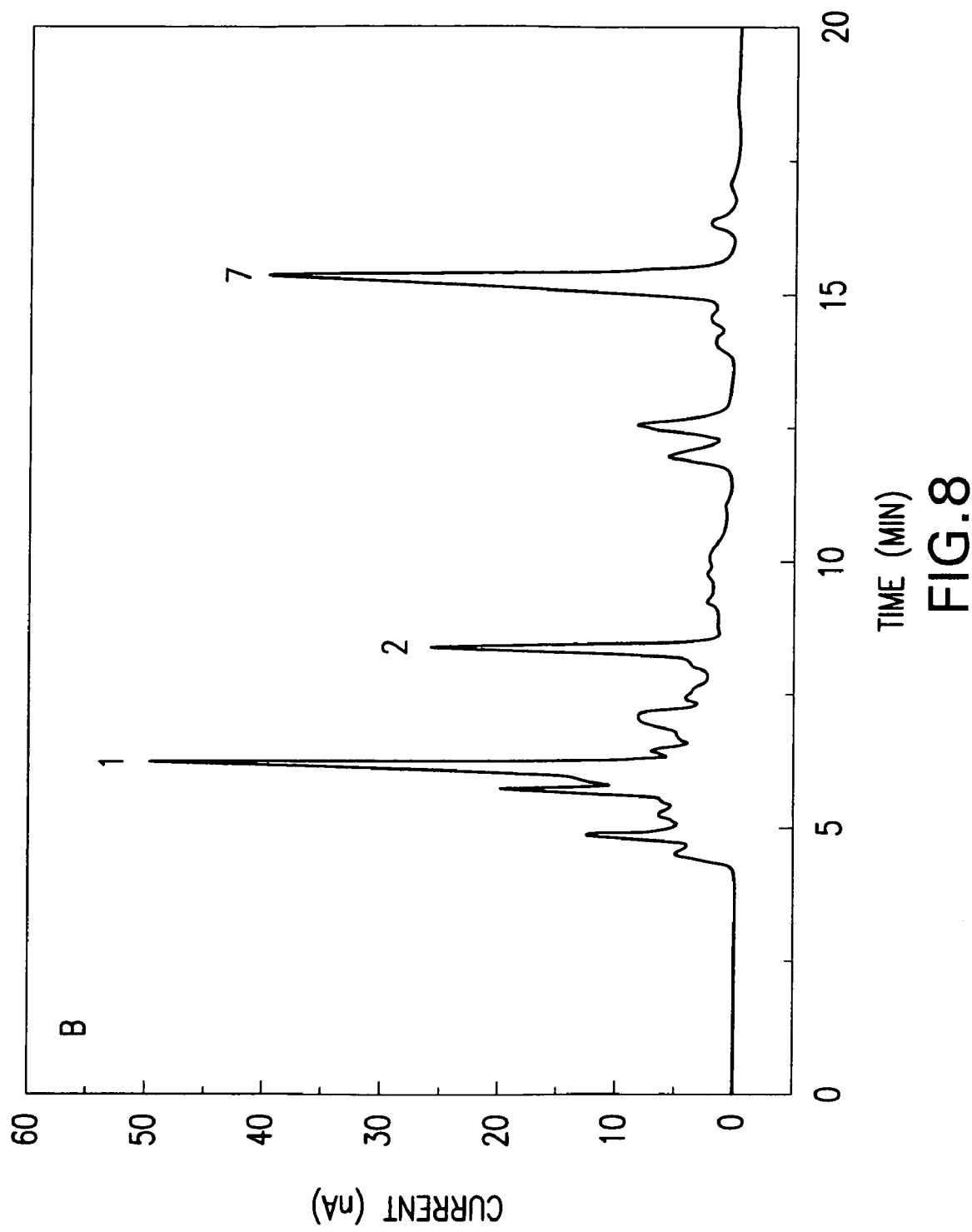

PLATFORM FOR ANALYSIS LIQUID SAMPLES

CROSS REFERENCE TO RELATED APPLICATIONS

This Application is a divisional of U.S. application Ser. No. 10/849,293, filed May 20, 2004, now abandoned, which claims the benefit of U.S. Provisional Patent Application No. 60/471,814, filed May 20, 2003, and U.S. Provisional Patent Application No. 60/527,936, filed Dec. 8, 2003.

BACKGROUND OF THE INVENTION

1. Field of the Invention

The present application relates to apparatus for sampling and analysis of analytes in a liquid sample. A liquid sample is pre-concentrated using a chromatographic column prior to analysis via a two stage analysis apparatus. A high-performance liquid chromatography system with ultra violet detection may be used in conjunction with electrochemical detection for the analysis of environmental contaminants, including explosive residues. The present invention also provides for on-site analysis of such contaminants. The present invention also provides for methods of analyzing the components of a liquid sample, including methods for on-site analysis.

2. Background of the Invention

Many environmental contaminants, including explosive residues, are known toxins and carcinogens, thus posing a threat to living species (J. Yinon, Toxicity and Metabolism of Explosives, CRC Press, Inc., Boca Raton (1990)). Current methodology for determining environmental contaminants is not always sensitive enough for trace analysis or selective enough for analysis in complex matrices. Presently, site assessment is typically done by collecting soil and ground water samples, storing them, and shipping them to specialty laboratories for analysis (J. Yinon and S. Zitrin, Modern Methods and Applications in Analysis of Explosives, John Wiley & Sons, LTD., New York, N.Y. (1993)). However explosive residues degrade over time, which can lead to inaccurate results when analyzing samples.

Several detectors have been coupled to high-performance liquid chromatography (HPLC) for the determination of explosive residues, including the ultra violet (UV) detectors, refractive index (RI) detectors, mass spectrometry (MS), and reductive dc amperometry. (J. Yinon and S. Zitrin, Modern Methods and Applications in Analysis of Explosives, John Wiley & Sons, Inc., New York (1993); A. M. Krstulovic and P. R. Brown, Reversed-Phase High-Performance Liquid Chromatography. Theory, Practice, and Biomedical Applications, John Wiley & Sons, Inc., New York, (1982); D. A. Martens and W. T. Frankenberger, Jr., *Chromatographia* 30:11-12 (1990); I. S. Krull, C. Selavka, and X-D. Ding, Proceedings of the International Symposium and the Analysis and Detection of Explosives, Federal Bureau of Investigation (FBI) Academy, Quantico, Mar. 29-31, 1983; A. Hilmi, et al., *J. Chromatogr. A* 844:97 (1999)). Both RI and UV detectors suffer from lack of sensitivity and selectivity due to the presence of interfering compounds in complex matrices. MS is complex, making it difficult to use it for performing quantitative work. Reductive amperometric techniques suffer from lack of sensitivity due to the reduction of dissolved oxygen present in the mobile phase and sample. In contrast, photo-assisted electrochemical detection (PAED) is very sensitive and selective and does not face the same limitations as reductive amperometry. HPLC-PAED involves first the separation of the analytes of interest, followed by the photolytic generation of a new species that can then be detected electrochemically (I. S. Krull, and W. R. LaCourse, Reaction Detection in Liquid Chromatography, Marcel Dekker, Inc., New York (1986)).

There exists therefore a need for a sampling system that can be used to analyze environmental liquid samples, including on-site analysis of liquid samples that would not require large sample volumes, or transportation of samples that can lead to degradation. The present application fulfills this need.

BRIEF SUMMARY OF THE INVENTION

In one embodiment, the present invention provides for an apparatus for sampling one or more analytes of a liquid sample, comprising: (a) one or more pre-concentration chromatographic columns that are capable of retaining the one or more analytes; (b) a solvent delivery system in fluid communication with the one or more pre-concentration chromatographic columns, wherein the solvent delivery system is capable of delivering a solvent that is capable of eluting the one or more analytes from the one or more pre-concentration chromatographic columns; (c) one or more analytical chromatographic columns in fluid communication with the one or more pre-concentration chromatographic columns, wherein the one or more analytical columns are capable of separating the one or more analytes; (d) a variable wavelength detector in fluid communication with the one or more analytical columns; and (e) an electrochemical detector in fluid communication with the variable wavelength detector. In suitable embodiments, the variable wavelength detector and the electrochemical detector may be connected in line or may be connected in parallel. In certain such embodiments, the electrochemical detector is a photo-assisted electrochemical detector. The apparatus of the present invention is suitably used to sample and analyze compounds selected from the group consisting of nitroso compounds, organic nitro compounds, organothiophosphates, polycyclic aromatic hydrocarbons (PAHs). and drug metabolites. In certain embodiments, the apparatus of the present invention is suitably used to sample and analyze explosive residues and mixtures of explosive residues.

In suitable embodiments of the present invention, the one or more pre-concentration chromatographic columns are capable of retaining explosive residues, but not capable of retaining salts or other contaminants. In certain embodiments, the one or more analytical chromatographic columns used in the apparatus are high-performance liquid chromatography columns. Suitably, the one or more pre-concentration chromatographic columns may be C18, 5 µm particle size columns and the one or more analytical chromatographic columns may be C18 reversed phase, 5 µm particle size columns.

In additional embodiments of the present invention, the apparatus may further comprise a sample loop in fluid communication with the one or more pre-concentration chromatographic columns. Suitably, this sample loop may be a 2 ml sample loop, and may be connected to a device for drawing a liquid sample from a reservoir.

The present invention also provides for methods for sampling one or more analytes of a liquid sample, comprising: (a) passing the liquid sample through one or more pre-concentration chromatographic columns, thereby retaining the one or more analytes on the one or more pre-concentration chromatographic columns and concentrating the one or more analytes; (b) delivering a solvent to the one or more pre-concentration chromatographic columns, thereby eluting the one or more analytes from the one or more pre-concentration chromatographic columns to give an eluate; (c) passing the eluate through one or more analytical chromatographic columns, thereby separating the one or more analytes; and (d) analyzing the separated one or more analytes in a variable wavelength detector and then in an electrochemical detector. In certain suitable embodiments, the methods of the present invention are used to analyze explosive residues or mixtures of explosive residues in a liquid sample.

In certain such embodiments of the methods present invention, a device is used to draw a liquid sample from a liquid reservoir into a sample loop prior to passing the liquid sample through the one or more pre-concentration chromatographic columns. The methods of the present invention may be used to sample environmental contaminants from any source, including ground water, and suitably the methods of the present invention are used for on-site analysis.

In other embodiments, the present invention also provides for methods for on-site sampling of one or more explosive residues of a liquid sample, comprising: (a) drawing the liquid sample from a liquid reservoir into a sample loop and holding the liquid sample in the sample loop; (b) passing the liquid sample from the sample loop through one or more pre-concentration chromatographic columns, thereby retaining the one or more explosive residues on the one or more pre-concentration chromatographic columns and concentrating the one or more explosive residues; (c) delivering a solvent to the one or more pre-concentration chromatographic columns, thereby eluting the one or more explosive residues from the one or more pre-concentration chromatographic columns to give an eluate; (d) passing the eluate through one or more high-performance liquid chromatography columns, thereby separating the one or more explosive residues on the one or more high-performance liquid chromatography columns; and (e) analyzing the separated one or more explosive residues in a variable wavelength detector and then in a photo-assisted electrochemical detector.

BRIEF DESCRIPTION OF THE DRAWINGS/FIGURES

The foregoing and other features and advantages of the invention will be apparent from the more particular description of the invention, as illustrated in the accompanying drawings. The drawings are not to scale.

FIG. 1: is a diagram of an embodiment of an apparatus for sampling analytes of a liquid sample in accordance with the present invention.

Figure 2:
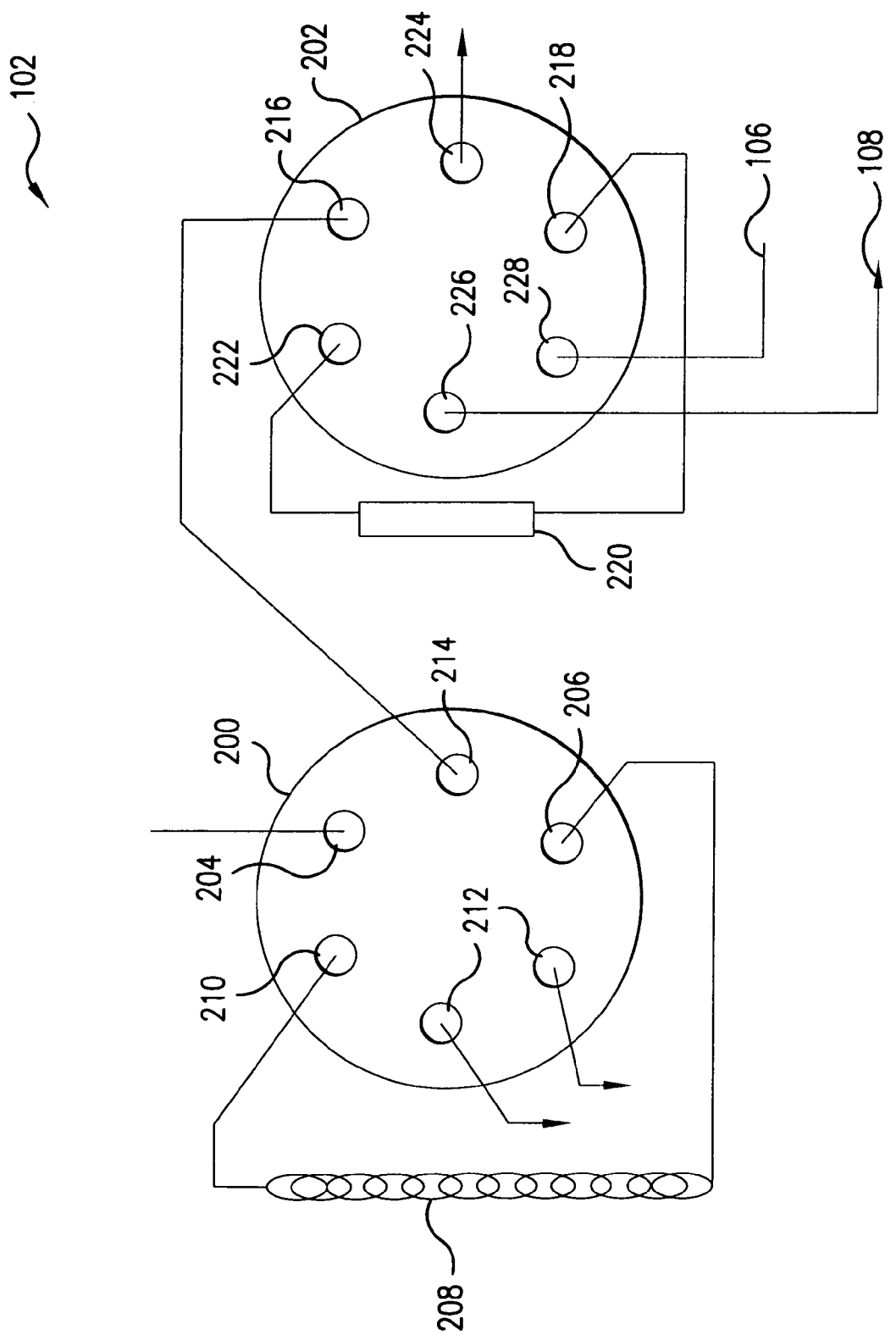

FIG. 2: is a diagram of an embodiment of a solid phase extraction unit for use in accordance with the present invention.

Figure 3:
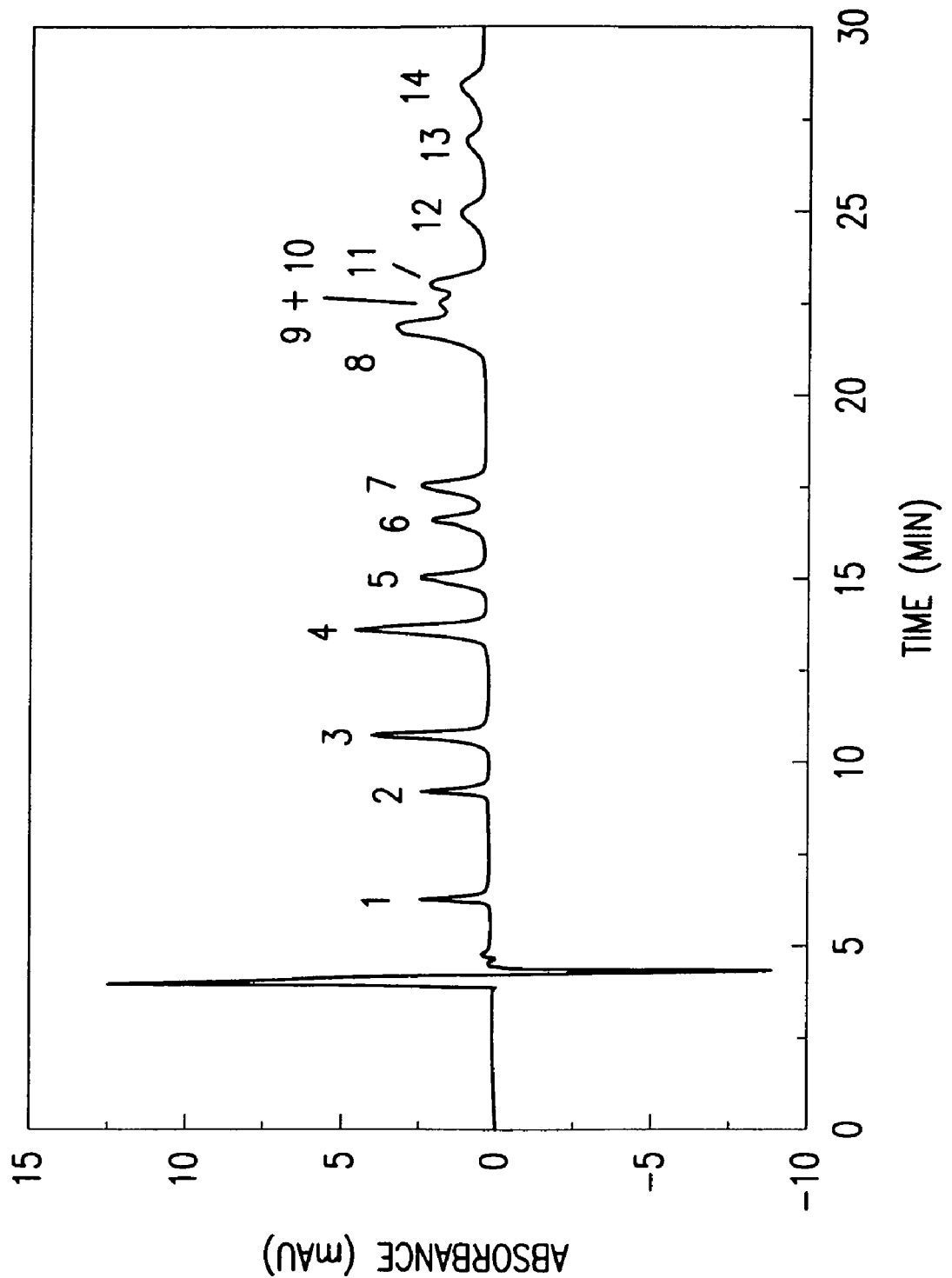

FIG. 3: is an ultra violet chromatogram of a mixture of explosive residues.

Figure 4:
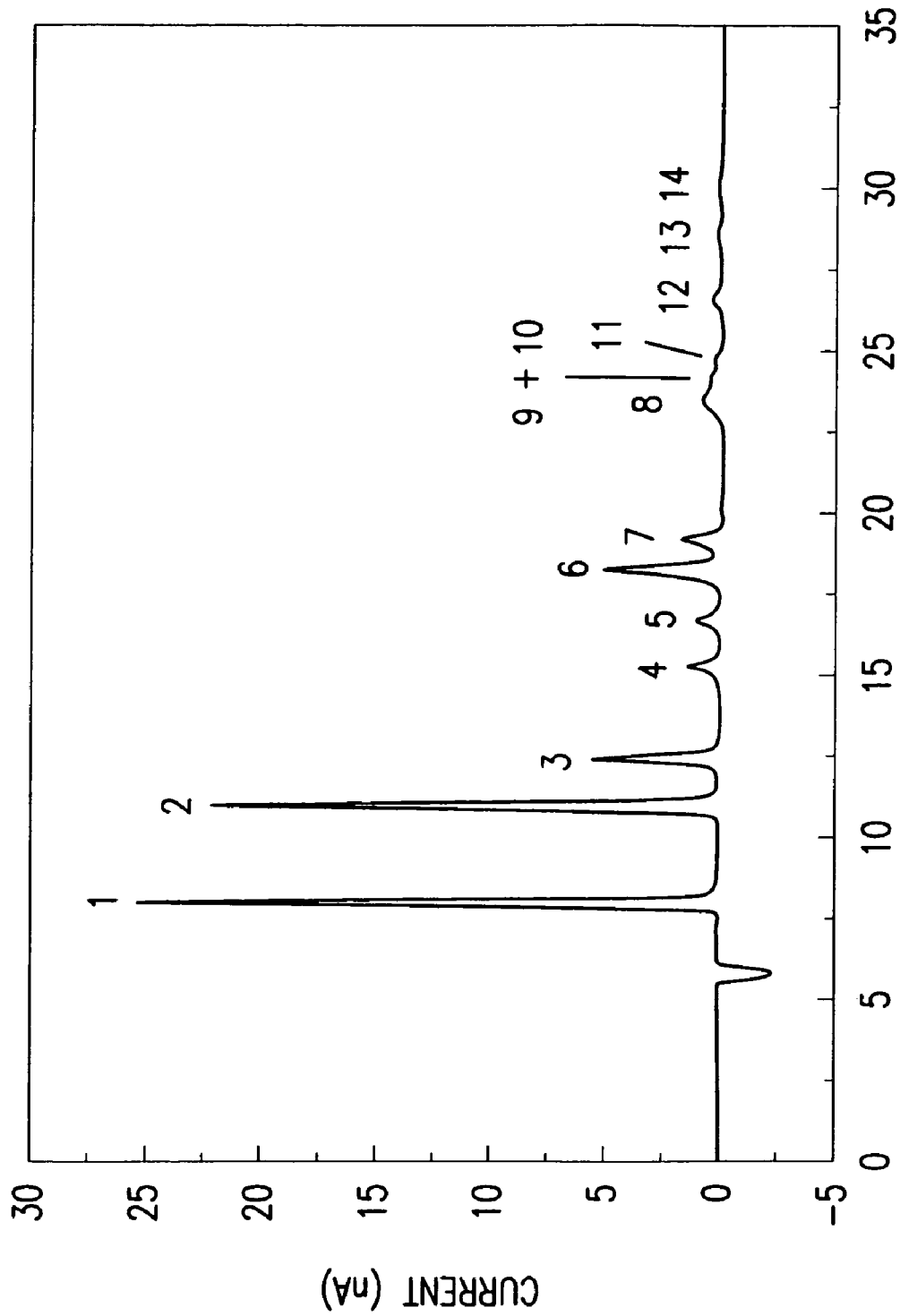

FIG. 4: is a photo-assisted electrochemical detection chromatogram of a mixture of explosive residues.

Figure 5:
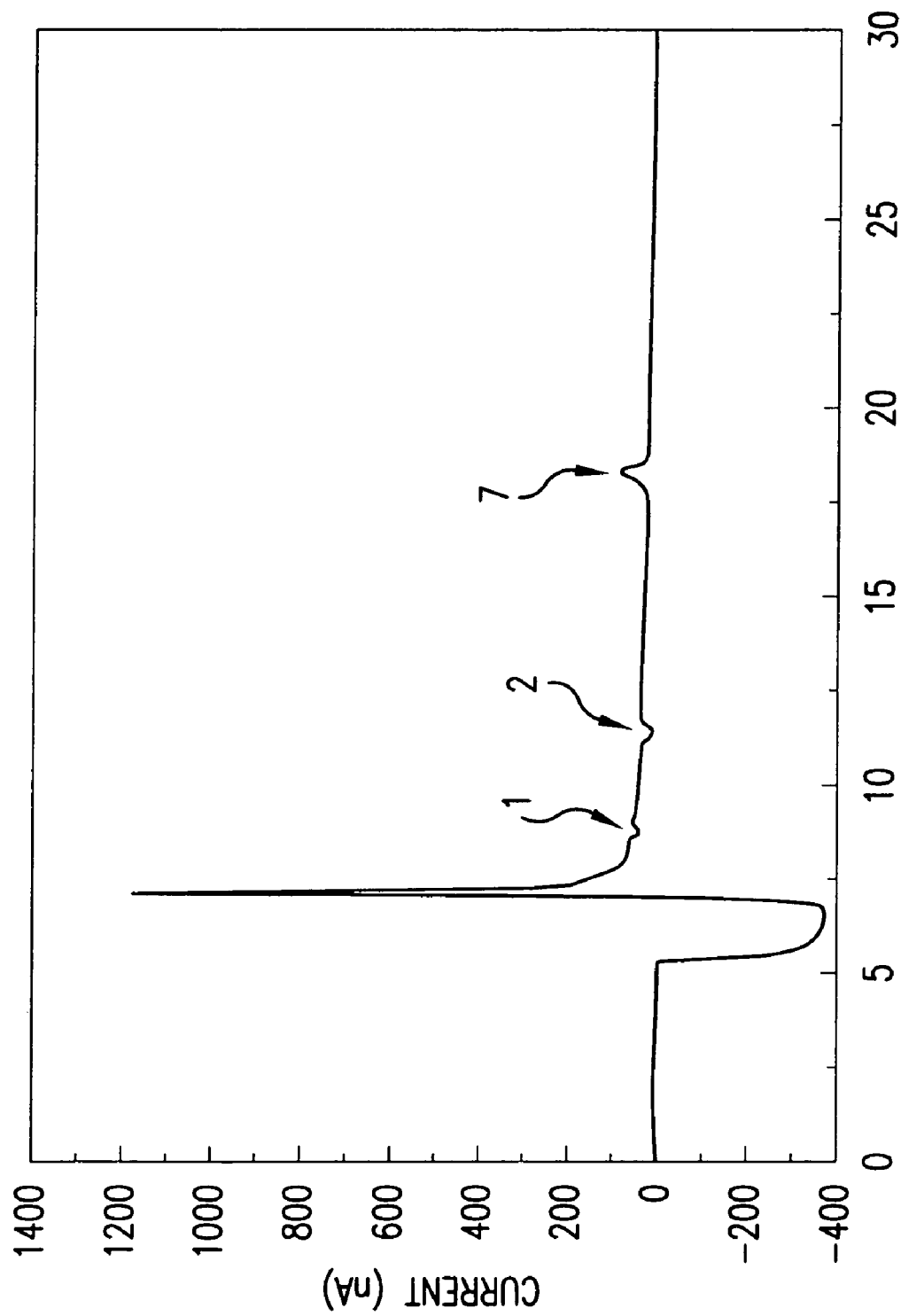

FIG. 5: is a photo-assisted electrochemical detection chromatogram of a mixture of explosive residues measured without using an on-line solid phase extraction unit.

Figure 6:
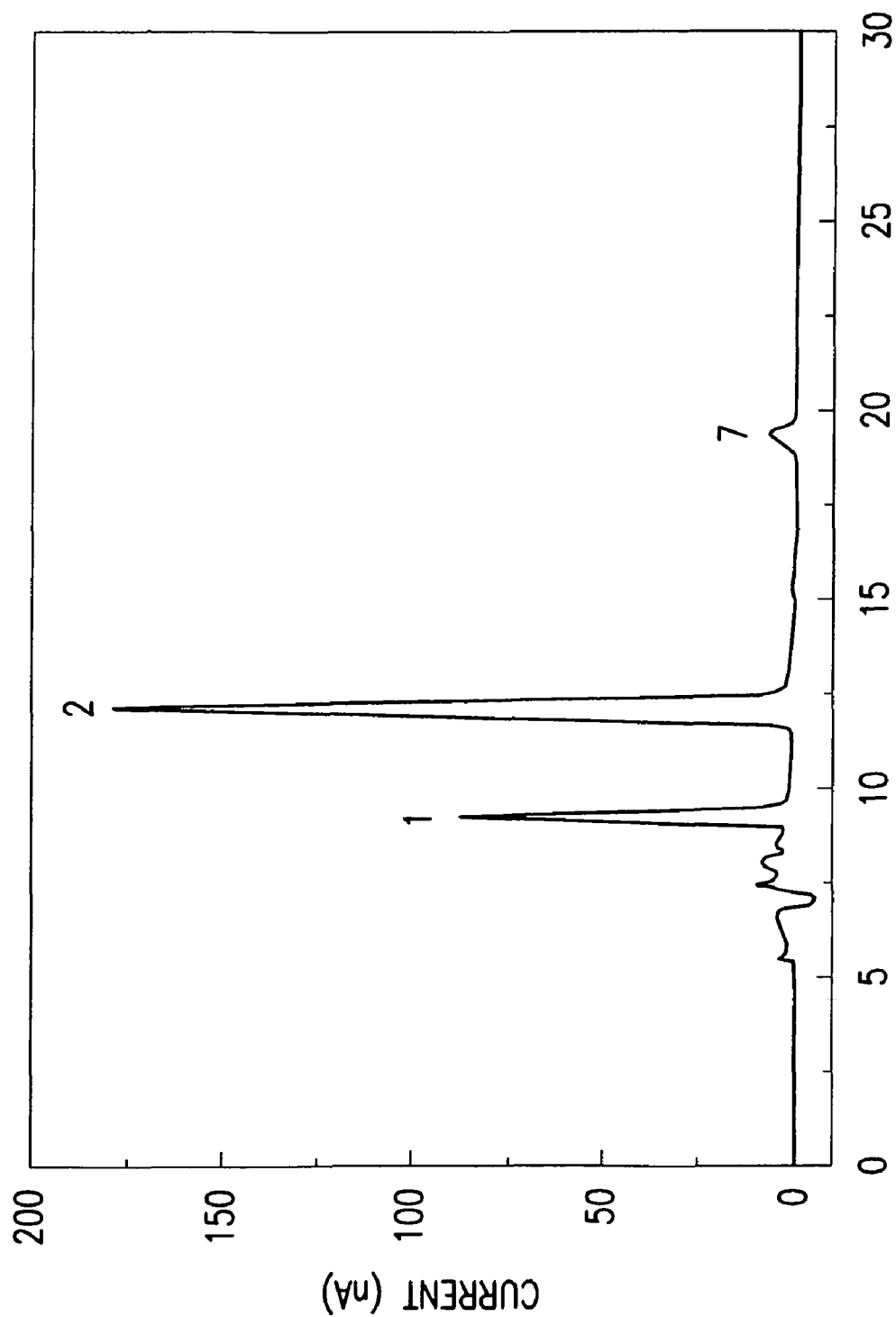

FIG. 6: is a photo-assisted electrochemical detection chromatogram of a mixture of explosive residues measured utilizing an apparatus in accordance with the present invention, including an on-line solid phase extraction unit.

Figure 7:
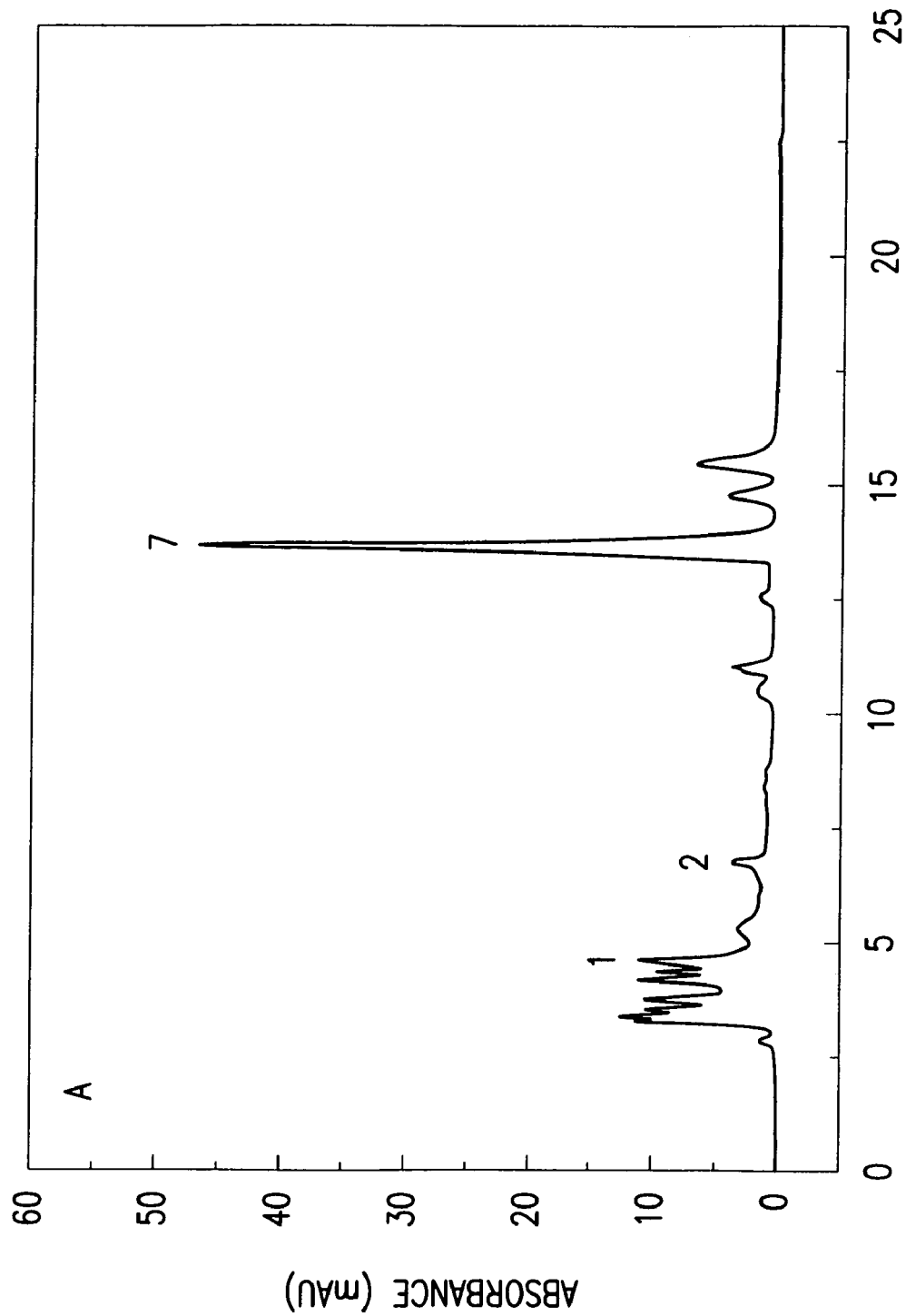

FIG. 7: is an ultra violet chromatogram of a mixture of explosive residues extracted from a soil sample.

FIG. 8: is photo-assisted electrochemical detection chromatogram of a mixture of explosive residues extracted from a soil sample.

DETAILED DESCRIPTION OF THE INVENTION

Suitable embodiments of the present invention are now described with reference to the figures, where like reference numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

In one embodiment, the present invention provides for an apparatus for sampling one or more analytes of a liquid sample. One certain such embodiment is represented in FIG. 1. Analysis apparatus 100 comprises a solid phase extraction (SPE) unit 102 shown in detail in FIG. 2. SPE unit 102 shown in FIG. 2 comprises sample injection valve 200 and solid phase extraction valve 202. Suitably, sample injection valve 200 is an electronically operated prep injector (Rheodyne, Rohnert Park, Calif.) and phase extraction valve 202 is an electronically operated, 6-port, 2-position valve (Rheodyne). Sample injection valve 200 comprises sample injection port 204 for injection of a liquid sample of interest. Sample injection port 204 may be connected to any suitable tubing that can deliver a liquid sample to the sample injection port. Any suitable tubing material may be used for the various tubing connections utilized in the apparatus of the present invention. Suitable tubing materials include, but are not limited to, stainless steel, copper, nylon, silicone, PolyEtherEtherKetone (PEEK® from Vitrex), Flourinated Ethylene-Propylene (FEP), Polytetrafluoroethylene (PTFE; TEFLON™ from DuPont), Perfluoroalkoxy (PFA), Viton® fluoroelastomer from DuPont, and Ethylene Tetrafluoroethylene (ETFE), TEFZEL® from DuPont.

In suitable embodiments of the present invention, sample input port 204 may be connected to a syringe, or other similar device, for injection of a liquid sample into the sample input port 204. In other suitable embodiments, sample input port 204 may be connected to a pumping system for drawing a liquid sample from a liquid reservoir. This pumping system may be a vertical profile ground water pumping system or any suitable type liquid pumping system known to the ordinarily skilled artisan. In certain such embodiments, a valve may be placed between the pumping system and the sample input port 204 in order to direct only desired liquid samples to analysis apparatus 100. In other such embodiments, one or more in-line filters may be placed between the valve and the sample input port 204 in order to filter particulates from the liquid sample prior to injection into sample input port 204. In certain such embodiments, these filters may be particle size filters, e.g. 5 μm, 1 μm and 0.45 μm particle size filters, and may be used in concert such that the liquid sample from the pumping system if first passed through the largest pore size filter (e.g. 5 μm) and then through filters of decreasing pore size (e.g. 1 μm followed by 0.45 μm) prior to injection in to sample input port 204. Sample input valve 204 may also be connected to solid phase extraction wash solution 104, suitably using the valve placed between the pumping system and the sample input port 204.

Following injection of a liquid sample into sample input port 204, the liquid sample flows out of port 210 to injection loop 208, and to port 206. In certain embodiments, the liquid sample may flow out of vent(s) 212 as waste. When it is desired that a liquid sample be analyzed, injection loop 208 allows for the retention of a volume of the liquid sample. In suitable embodiments, injection loop 208 may be any volume that retains a sufficient liquid volume for analysis. Suitably, injection loop 208 may comprise a volume including, but not limited to, about 100 µl, about 200 µl, about 500 µl, about 1 ml, about 2 ml, about 3 ml, about 4 ml, about 5 ml, about 10 ml, about 15 ml, about 20 ml, about 30 ml, about 40 ml, about 50 ml, about 100 ml, about 200 ml, about 500 ml and any range within these values. Suitably, injection loop 208 has a volume of about 2 ml. As used herein, when referring to any numerical value, "about" means a value of ±10% of the stated value (e.g. "about 100 ml" encompasses a range of sizes from 90 ml to 110 ml, inclusive).

Once a desired liquid sample is collected in injection loop 208, sample injection valve 200 may be activated so as to allow solid phase extraction wash solution 104 to flow into sample input port 204 and carry the liquid sample in injection loop 208 to port 206 to output port of sample injection valve 214 and into input port of phase extraction valve 216. As noted above, all fluid connections between the various components of analysis apparatus 100 may utilize any suitable tubing and connections known to the ordinarily skilled artisan.

While in suitable embodiments, solid phase extraction unit 102 may comprise both sample injection valve 200 and solid phase extraction valve 202, in certain embodiments, sample injection valve 200 may not be required.

Rather a liquid sample can be directly injected into solid phase extraction valve 202 at input port to phase extraction valve 216, e.g. via a syringe, and then followed by solid phase extraction wash solution 104.

Following injection of the liquid sample into input port to solid phase extraction valve 216, either from sample injection valve 200, or from a syringe, the liquid sample carried by solid phase extraction wash solution 104 then flows to input port 222, and then on to pre-concentration chromatographic column 220. Suitably, phase extraction column 220 is a miniature chromatographic column that will retain one or more analytes of interest on the column under weak solvent solutions, while allowing highly polar species to pass as waste. Any suitable chromatography column known to the ordinarily skilled artisan may be used in the practice of the present invention (e.g. a C18, 5 µm particle size column, Ansys Technologies, Inc., Lake Forest, Calif.). Suitable solvents for use as solid phase extraction wash solution 104 are any weak solvents that allow for the one or more analytes of interest to remain bound to the column, but allow for contaminants such as salts and other highly polar species to pass through pre-concentration chromatographic column 220 as waste. Suitable wash solutions include weak solvents such as, but not limited to, methanol in a solution of acetate and sodium chloride, acetonitrile, and any other weak solvent known to the ordinarily skilled artisan. Waste from pre-concentration chromatographic column 220 flows to output port 218, and then out of the SPE unit 102 through vent 224. Use of a pre-concentration chromatographic column removes salts and other contaminants that generate a large background current and mask the analytes (e.g. explosive residues) of interest.

After an optimized "wash" time, output port of sample injection valve 214 is closed, and wash solution input port 228 is opened to allow analytical solvent 112 supplied by analytical solvent pump 114 to flow from wash solution input 106 into wash solution input port 228, to output port 218, through pre-concentration chromatographic column 220 to create an eluate comprising the one or more analytes. This eluate is then passed to input port 222, and then to output port of phase extraction valve 226. This allows for analytical solvent 112 to backflush through pre-concentration chromatographic column 220 and then to output to analytical device 108, resulting in partial fractionation and concentration of the one or more analytes of the liquid sample. Suitable solvents for use as analytical solvent 112 include any polar solvent known to the ordinarily skilled artisan that would allow elution of the one or more analytes that have been retained on pre-concentration column 220. Suitable solvents include, but are not limited to, methanol in acetate buffer, acetonitrile and any polar solvent known to the ordinarily skilled artisan. As a result, the present invention allows for on-line sample preparation via the use of SPE unit 102, while eliminating the need for the "salting-out" extraction procedure required by EPA Method 8330.

In suitable embodiments of the present invention, the eluate comprising the one or more analytes is then directed to pneumatic injector 118, prior to being passed through one or more analytical chromatographic columns 116 in order to separate the one or more analytes. In certain such embodiments, analytical chromatographic column 116 is a high-performance liquid chromatography column. While FIG. 1 illustrates the use of one analytical column in the application of the present invention, multiple analytical columns may be used in the apparatus and methods of the present invention. Any chromatography column known to the ordinarily skilled artisan that allows for separation of analytes of a liquid solution may be used as analytical column(s) 116 in the apparatus and methods of the present invention, including 4.6×250 mm C18 reversed phase, 5 µm particle size chromatography columns, ion exchange columns, normal phase columns and size exclusion columns. Analytical chromatographic columns useful in the apparatus and methods of the present invention may be obtained from manufacturers such as Perkin Elmer (Boston, Mass.), Varian, Inc. (Palo Alto, Calif.), Vydac (Hesperia, Calif.), Hamilton Co. (Reno, Nev.), and Waters Corp. (Milford, Mass.). In certain suitable embodiments, pneumatic injector 118 may comprise injection loop 110 for use with direct injection of liquid samples. In such suitable embodiments, the liquid sample is not processed through SPE unit 102, but rather directly injected into one or more analytical chromatographic columns 116 prior to analysis. Suitably, injection loop 110 may comprise a volume including, but not limited to, about 100 µl, about 200 µl, about 500 µl, about 1 ml, about 2 ml, about 3 ml, about 4 ml, about 5 ml, about 10 ml, about 15 ml, about 20 ml, about 30 ml, about 40 ml, about 50 ml, about 100 ml, about 200 ml, about 500 ml and any range between these values. Suitably, injection loop 110 has a volume of about 100 µl.

Following injection of the eluate into analytical chromatography column 116, the one or more analytes are separated on the column, and then directed to one or more analyzers in fluid communication with column 116. In FIG. 1, one embodiment of the present invention is represented in which a first analyzer may be variable wavelength detector 120. Suitably, variable wavelength detector 120 will be an ultraviolet/visible (UV/Vis) variable wavelength detector, though other similar detectors may be used in the practice of the present invention. Following variable wavelength detector 120, the one or more analytes are directed to photochemical reactor 122, followed by electrochemical cell 124 and then electrochemical detector 126. Components 122, 124 and 126 make up the photo-assisted electrochemical detection (PAED) apparatus. Photochemical reactor 122 is used to photo reduce the one or more analytes. The photo reduced analytes are then directed into electrochemical cell 124 where they are oxidized, and the output current is monitored by electrochemical detector 126, prior to leaving the analysis apparatus via waste output 128. (For additional information regarding electrochemical detection, see Krull, I. S. "Reaction Detection in Liquid Chromatography," Marcel Dekker, Inc., New York (1986).) Each of these units (122, 124, 126) are suitably connected in fluid communication with one another, and suitably may be connected in-line and in fluid communication with variable wavelength detector 120, or in other suitable embodiments may be connected in parallel with variable wavelength detector 120.

Variable wavelength detector 120 and electrochemical detector 126 are connected to data output device 130 which displays both ultra violet chromatograms and photo-assisted electrochemical detection (PAED) chromatograms of the one or more analytes. Although analytes can be determined with both detectors, the PAED is, on average, more sensitive than the variable wavelength (UV) detector (especially when analyzing explosive residues). UV detection is often considered less selective than EC detection due to the large number of analytes that absorb UV light. EC detection is selective in that only those analytes that are EC active under the applied potential will respond, and EC detection is often more sensitive than UV detection. However, having these two detectors in-line together provides the advantage of better analyte identification by allowing the comparison of retention times of analytes versus standards on two detectors and the comparison of response ratios (EC signal divided by UV signal) of analytes verses standards. Duel detector confirmation vastly improves the selectivity of the HPLC system. For several important compounds of interest, such as HMX, RDX, and TNT, the lower limits of detection achieved electrochemically are 10 to 1000 times less than those achieved by UV, and this is very advantageous in trace analysis or when samples are available in limited amounts.

The present invention also provides for methods for sampling one or more analytes of a liquid sample using the apparatus of the present invention, comprising: (a) passing the liquid sample through one or more pre-concentration chromatographic columns, thereby retaining the one or more analytes on the one or more pre-concentration chromatographic columns and concentrating the one or more analytes; (b) delivering a solvent to the one or more pre-concentration chromatographic columns, thereby eluting the one or more analytes from the one or more pre-concentration chromatographic columns to give an eluate; (c) passing the eluate through one or more analytical chromatographic columns, thereby separating the one or more analytes; and (d) analyzing the separated one or more analytes in a variable wavelength detector and then in an electrochemical detector.

In suitable embodiments, the apparatus and methods of the present invention may be used to analyze one or more analytes, including but not limited to, nitroso compounds, organic nitro compounds, organothiophosphates, PAHs and drug metabolites. Suitably, the one or more analytes will be one or more explosive residues or a mixture of explosive residues. Non-limiting examples of explosive residues that can be sampled and analyzed using the apparatus and methods of the present invention include Octagen (HMX), Hexagen (RDX), 1,3,5-trinitrobenzene (1,3,5-TNB), 1,3-dinitrobenzene(1,3-DNB), Nitrobenzene (NB), Methyl-2,4, 6-trinitrophenylnitramine (Tetryl), 2,4,6-trinitrotoluene (2,4, 6-TNT), 4-amino -2,6-dinitrotoluene (4-A-2,6-DNT), 2,6-dinitrotoluene (2,6-DNT), 2-amino -4,6-dinitrotoluene (2-A-4,6-DNT), 2,4-dinitrotoluene (2,4-DNT), 2-nitrotoluene (2-NT), 4-nitrotoluene (4-NT) and 3-nitrotoluene (3-NT).

Simply by changing or modifying the one or more pre-concentration chromatographic columns, the solid phase extraction wash solution, the analytical solvent, the one or more analytical columns, and/or the one or more detectors, the apparatus and methods of the present invention may also be used to sample and analyze other analytes of interest. Other analytes of interest may include metals, polyaromatic hydrocarbons, perchlorates, organothiophosphates, nitrosamines, and penicillins.

In suitable embodiments, the apparatus and methods of the present invention may be modified so as to allow for sampling and analysis of drug metabolites in liquid solutions. Such metabolites include drug metabolites such as, but not limited to glucuronide metabilites In certain such suitable embodiments, the apparatus and methods of the present invention may be applied to the sampling and analysis of drug metabolites by changing or modifying the one or more pre-concentration chromatographic columns, the solid phase extraction wash solution, the analytical solvent, the one or more analytical columns, and/or the one or more detectors using the variations described throughout. Suitably, both the variable wavelength detector and the electrochemical detector will be utilized.

In other embodiments, the present invention provides for on-site sampling of one or more explosive residues of a liquid sample using the apparatus of the present invention, comprising: (a) drawing the liquid sample from an on-site liquid reservoir into a sample loop and holding the liquid sample in the sample loop; (b) passing the liquid sample from the sample loop through one or more pre-concentration chromatographic columns, thereby retaining the one or more explosive residues on the one or more pre-concentration chromatographic columns and concentrating the one or more explosive residues; (c) delivering a solvent to the one or more pre-concentration chromatographic columns, thereby eluting the one or more explosive residues from the one or more pre-concentration chromatographic columns to give an eluate; (d) passing the eluate through one or more high-performance liquid chromatography columns, thereby separating the one or more explosive residues on the one or more high-performance liquid chromatography columns; and (e) analyzing the separated one or more explosive residues in a variable wavelength detector and then in a photo-assisted electrochemical detector.

In one embodiment, the present invention provides for a sampling apparatus that can be used on site, i.e. as a field-compatible apparatus. In certain such embodiments of the present invention, the methods and apparatus may be used to sample ground water or other liquid samples directly at the sample site without the need to collect a large sample volume or transport a sample from the site to an analysis laboratory. This reduces the cost of analysis, the possibilities of degradation of analytes, and the risks associated with multiple operators contacting toxic substances.

The apparatus and methods of the present invention may also be extended to analysis of contaminated soils through the use of pressurized fluid extraction (PFE) (see B. E. Richter, et al., *Anal. Chem.* 68:1033-1039 (1996)). Such extraction may be performed using solvents known to the ordinarily skilled artisan, including but not limited to, methanol and acetone, and at various temperatures over the range of about 90° C. to about 200° C. (see B. E. Richter, et al.).

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Analysis of Explosive Residues in a Liquid Sample

Instrumentation

A Dionex DX-500 HPLC (Dionex Corporation, Sunnyvale, Calif.), comprises analytical column 116, variable wavelength detector 120 analytical solvent pump 114 and electrochemical detector 126. Analytical solvent 112 is 50% methanol in 20 mM acetate buffer, pH=4.5, delivered by analytical solvent pump 114 at a flow rate of 1.0 mL/min. Pneumatic injector 118 is fitted with a 100 µL injection loop 110. Analytical column 116 is a C18 reversed phase column, 5 µm particle size, 4.6×250 mm (Vydac, Hesperia, Calif.), which is placed in a column oven set at 30° C. A Phenomenex SecurityGuard column fitted with a 4 mL×3.0 mm ID C8 cartridge may also be used (Phenomenex, Torrance, Calif.). Variable wavelength detector 120 is in-line following the column, and photochemical reactor 122 (PHRED™, Photochemical Reactor for Enhanced Detection, Aura Industries, Inc., New York, N.Y.) is placed after the UV detector. The PHRED™ contains a PTFE™ reactor coil that is 25 m in length and 0.25 mm in internal diameter with a volume of 1.25 mL, and the bulb in the reactor is a 254 nm UV bulb. The analytes of interest, after passing through the variable wavelength detector 120, then flow through the knitted reactor coil and are irradiated to produce photoproducts that are determined at the electrochemical detector 126. This component adds an additional mode of selectivity in that the compounds of interest respond uniquely under these conditions; that is, they must undergo photo derivatization at the given wavelength and they must respond to the applied potential in the electrochemical cell. Thin-layer electrochemical cell 124 is next in the flow path. The electrochemical cell is fitted with a 1 mm diameter glassy carbon working electrode and a silver-silver chloride reference electrode, while the body of the cell serves as the auxiliary electrode. The resultant data is represented by dual chromatograms on a Tangent computer using Dionex PeakNet software version 5.21.

Solid Phase Extraction (SPE) unit 102 consists of two electronically operated valves, one 6-port, 2-position valve 202 (Rheodyne labPRO model RP750-100, version-01, Rheodyne, Rohnert Park, Calif.) and one Prep Injector 200 (Rheodyne labPRO model RP750-102, version-01, Rlwodyne). The lines connecting the ports represent PTFE tubing. The 6-port, 2-position injection valve further comprises a short column in-line. The injectors are operated by the GP40 pump through relay controls written in the method. The prep injector is fitted with a 2 mL injection loop. The short column on the 6-port, 2-position valve is a C18 column with a 5 µm particle size, 4.6×75 mm (MetaSil™ 0381-075×46, Ansys Technologies, Inc., Lake Forest, Calif.). SPE wash solution 104 is 7.5% methanol in a solution of 20 mM acetate and 0.5M sodium chloride and is delivered to the unit by an isocratic pump (Model 510, Waters Corporation, Milford, Mass.) at a flow rate of 1.0 mL/min.

Reagents And Solutions

Table 1 lists the name, peak number, abbreviation, EPA classification (Mix A or B), and Restek classification (1 or 2) of all the explosives of EPA Method 8330. Standard solutions (Restek Corporation, Bellcronte, Pa.) were purchased as mixtures denoted as either Calibration MIX #1 or Calibration Mix #2 at concentrations of 1000 µg/mL, each in 1 mL acetonitrile. Standard solutions were stored in a refrigerator at 4° C. All stock solutions were prepared daily in deionized water. Sodium acetate trihydrate, sodium chloride, and methanol (HPLC grade) were purchased from Fisher Scientific (Pittsburgh, Pa.). Ground water was obtained from Columbia Technologies (Baltimore, Md.) and stored at 4° C. until use. Certified soil samples were obtained from Environmental Resource Associates (Arvada, Colo.) and stored at 4° C. until use.

TABLE 1

Peak legend for each chromatogram.

| Peak # | Explosive | Abbreviation | EPA Classification | Restek Mix |
|---|---|---|---|---|
| 1 | Octagen | HMX | A | 1 |
| 2 | Hexagen | RDX | A | 1 |
| 3 | 1,3,5-trinitrobenzene | 1,3,5-TNB | A | 1 |
| 4 | 1,3-dinitrobenzene | 1,3-DNB | A | 1 |
| 5 | Nitrobenzene | NB | A | 1 |
| 6 | Methyl-2,4,6-trinitrophenyl-nitramine | Tetryl | B | 2 |
| 7 | 2,4,6-trinitrotoluene | 2,4,6-TNT | A | 1 |
| 8 | 4-amino-2,6-dinitrotoluene | 4-A-2,6-DNT | B | 2 |
| 9 | 2,6-dinitrotoluene | 2,6-DNT | B | 2 |
| 10 | 2-amino-4,6-dinitrotoluene | 2-A-4,6-DNT | A | 2 |
| 11 | 2,4-dinitrotoluene | 2,4-DNT | A | 1 |
| 12 | 2-nitrotoluene | 2-NT | B | 2 |
| 13 | 4-nitrotoluene | 4-NT | B | 2 |
| 14 | 3-nitrotoluene | 3-NT | B | 2 |

Safety Considerations

Nitro explosives are known toxins and carcinogens and should be handled with gloves in a fume hood. Skin and eye contact and ingestion should be avoided.

Results and Discussion

Optimization of Direct Injection Method.

The system was first set-up for direct injection of samples on the analytical system using the 100 µL injection loop. Parameters that must be optimized to achieve maximum sensitivity from PAED include the detection potential and the flow rate (or residence time in the photochemical reactor). In order to optimize the PAED detection potential, the technique of hydrodynamic voltammetry (HDV) at a constant flow rate of 1.0 mL/min was employed. The resulting data was plotted as S/N (analytical signal-to-noise ratio) versus applied potential. HDV experiments were carried out using the PHRED at three different buffer pH values (3.5, 4.5, and 5.5) over a range of 0.2 V to 1.0 V, allowing selection of optimum pH and applied potential simultaneously. It was determined that the explosive residues show minimal response below an applied potential of 0.8 V, while the analytes show a maximum signal-to-noise ratio at 1.0 V. Beyond 1.0 V, however, the analyte response begins to decrease while the noise increases, thus decreasing the signal-to-noise ratio. All EPA Method 8330 explosives responded in a similar manner. Varying the pH showed little effect, so a pH of 4.5 and applied potential of 1.0 V were chosen as optimum values for PAED.

The optimal residence time in the photochemical reactor, necessary to achieve the maximum generation of photoproducts, is determined by holding the potential constant and varying the flow rate for each injection of a mixture of analytes. Here, the potential used was 1.0 V and the pH=4.5, and the flow rate was varied between 0.4 and 1.4 mL/min. It was observed that if the flow rate is too slow and the analytes are in the photochemical reactor too long, photochemical degradation of the desired product may occur. This is evident at flow rates below about 0.8 mL/min. The analytes show a maximum signal-to-noise ratio at 1.0 mL/min, and all faster flow rates do not allow enough time for the generation of the maximum amount of photoproducts. All nitro compounds responded similarly, and an optimum flow rate of 1.0 mL/min was chosen.

Optimization of On-Line SPE.

On-line SPE uses a pre-concentration column that retains the analytes of interest under weak solvent conditions while allowing highly polar species to pass as waste. A stronger solvent is then passed through the miniature column and elutes the analytes of interest. By this method, partial fractionation and concentration of the sample is achieved using simple chromatographic principles. On-line SPE allows on-line sample preparation while eliminating the need for the "salting-out" extraction procedure required by EPA Method 8330.

In order to perform on-line SPE with a sample, it is loaded in the 2 mL injection loop. Then, the prep injector is electronically actuated, allowing the SPE solvent to flow through the loop and carry the sample to the precolumn. After an optimized "wash" time, the prep injector is returned to the load position while the 6 port valve is turned to the inject position simultaneously. This allows the HPLC mobile phase (analytical solvent) to backflush through the pre-concentration column and into the analytical column. This valve remains open throughout the entire chromatographic run. At the end of the run, a five-minute wash with 80% methanol cleans the columns before the next injection.

In order to achieve maximum sample clean-up without washing the explosive residues off of the pre-concentration column, it was necessary to wash the sample onto the pre-concentration column for as long as possible. This was simply done by removing the analytical column, connecting the pre-concentration column directly to the UV detector, injecting a standard, allowing it to be washed through the pre-concentration column with the weak solvent, and monitoring the detector for the time that the first explosive residue eluted. A wash time of 6.0 minutes at a flow rate of 1.0 mL/min was chosen.

A solid phase extraction wash solvent of 7.5% methanol in a solution of 20 mM acetate and 0.5 M sodium chloride was determined experimentally. The methanol was needed in a small amount to create a weak solvent, and the acetate was added to make the wash solvent similar to the HPLC mobile phase. Sodium chloride was used to mimic the "salting out" extraction process of EPA Method 8330. A blank ground water sample was used to determine what concentrations of salts and methanol would give the greatest sample cleanup.

Direct Injection of Explosive Residues.

The UV and PAED chromatograms under optimized separation and detection conditions are shown in FIG. 3: UV and FIG. 4: PAED. These figures represent the first mode of selectivity—comparison of retention times of standards versus analytes in a sample on two detectors rather than UV only (as in EPA Method 8330). FIG. 4 is scaled so that peaks 12, 13, and 14 are at the same sensitivity as those in the UV chromatogram. Upon examination of the two chromatograms, the increased sensitivity achieved by PAED for the nitramines (HMX and RDX) and other compounds such as tetryl and TNT is clearly demonstrated.

The response ratios for standards, another mode of selectivity stemming from the use of two detectors, are presented in table 2 for selected explosives. They are found by dividing the EC signal by the UV signal for a particular analyte. In addition to comparing retention times between analytes in a sample and standards on two detectors and a lamp on/lamp off approach, the ratios of a possible analyte can be compared to that of a standard analyte to help identify the explosive.

The figures of merit for the model compounds are presented in table 3A. These were determined using the direct injection method with the 100 µL injection loop, and all solutions were made in deionized water. The figures of merit for 2,6-DNT and 2-A-4,6-DNT were tabulated by running calibration curves for each of these compounds separately. When comparing limits of detection, PAED is more sensitive than UV detection for almost all of the model compounds. For some of the more common explosives, there is an approximate 1000-fold and 100-fold increase in sensitivity for HMX and RDX, respectively, and an approximate 100-fold and 10-fold increase in sensitivity for tetryl and TNT, respectively, over UV detection.

TABLE 2

Response ratios for listed explosives.

| Explosive | Response ratio, direct injection, EC/UV | Response ratio, SPE, EC/UV |
|---|---|---|
| HMX | 31.76 ± 3.51 | 76.43 ± 2.00 |
| RDX | 31.35 ± 2.97 | 64.60 ± 1.65 |
| Tetryl | 10.67 ± 1.20 | 20.42 ± 0.66 |
| TNT | 7.42 ± 0.18 | 6.81 ± 0.26 |

TABLE 3A

Analytical figures of merit using the direct injection method.

| Explosive | Detection | LOD[a] (ug/L) | m | b | R[b] | LOQ[b] (ug/L) | % RSD n = 7 |
|---|---|---|---|---|---|---|---|
| 1 | UV | 2 | 90673 | 68 | 0.99949 | 4 | 0.80 |
|   | PAED | 0.007 | 19602576 | 10417 | 0.99935 | 0.02 | 4.08 |
| 2 | UV | 2 | 142265 | 272 | 0.99915 | 4 | 1.44 |
|   | PAED | 0.02 | 20120735 | 13029 | 0.99950 | 0.08 | 2.26 |
| 3 | UV | 1 | 306047 | 266 | 0.99908 | 3 | 1.75 |
|   | PAED | 0.06 | 5791715 | 6931 | 0.99955 | 0.2 | 2.43 |
| 4 | UV | 1 | 467947 | 376 | 0.99980 | 2 | 0.85 |
|   | PAED | 0.5 | 1978307 | 325 | 0.99996 | 2 | 3.65 |
| 5 | UV | 0.9 | 325421 | −164 | 0.99997 | 3 | 2.88 |
|   | PAED | 0.3 | 2032216 | −4097 | 0.99974 | 1 | 5.00 |
| 6 | UV | 2 | 235262 | 228 | 0.99905 | 5 | 1.47 |
|   | PAED | 0.03 | 9040367 | 3099 | 0.99986 | 0.3 | 0.91 |

TABLE 3A-continued

Analytical figures of merit using the direct injection method.

| Explosive | Detection | LOD[a] (ug/L) | m | b | $R^b$ | LOQ[b] (ug/L) | % RSD n = 7 |
|---|---|---|---|---|---|---|---|
| 7 | UV | 2 | 328575 | 328 | 0.99975 | 4 | 1.88 |
|   | PAED | 0.1 | 3141376 | 250 | 0.99989 | 1 | 2.83 |
| 8 | UV | 1.8 | 238989 | −24 | 0.99991 | 6 | 0.95 |
|   | PAED | 2 | 964574 | 1460 | 0.99990 | 6.8 | 1.76 |
| 9 | UV | 2 | 226891 | −19 | 0.99990 | 6.7 | 1.52 |
|   | PAED | 2 | 1259294 | 1986 | 0.99994 | 6.7 | 1.46 |
| 10 | UV | 1 | 356023 | −289 | 0.99994 | 3.2 | 0.50 |
|    | PAED | 3.5 | 504355 | −839 | 0.99992 | 11.5 | 0.46 |
| 11 | UV | 1 | 463620 | 66 | 0.99993 | 3.5 | 0.80 |
|    | PAED | 2 | 1458181 | −593 | 0.99990 | 6.4 | 1.63 |
| 12 | UV | 3 | 191530 | −461 | 0.99952 | 7 | 3.41 |
|    | PAED | 0.3 | 2011157 | −5032 | 0.99997 | 3 | 5.35 |
| 13 | UV | 4 | 166670 | −591 | 0.99930 | 12 | 2.01 |
|    | PAED | 1 | 697940 | −3275 | 0.99915 | 3 | 6.70 |
| 14 | UV | 5 | 210125 | −1010 | 0.99927 | 15 | 2.77 |
|    | PAED | 3 | 440613 | −3193 | 0.99910 | 11 | 5.52 |

[a]LODs are calculated at S/N = 3.
[b]LOQs are calculated at S/N = 10.

With the optimized system, the limits of detection are much lower than those previously described in the literature (I. S. Krull, et al., *"Proceedings of the International Symposium on the Analysis and Detection of Explosives,"* Federal Bureau of Investigation Academy, Quantico, Va. (1983); I. S., Krull, et al., *Reaction Detection in Liquid Chromatography*, Marcel Dekker, Inc., New York, N.Y. (1986); I. S., Krull, et al., *Am. Lab.* 57-65 (1983); K. Bratin, et al., *Am. Lab.* 33-62 (1984); I. S. Krull, et al., *LC Mag.* 2(3):214-221 (1984); I. S. Krull, et al., *Cur. Sep.* 5:57-62 (1984); I. S. Krull, et al., *LCGC* 7(9): 758-769 (1989); I. S. Krull, and C. M. Selavka, *J. of Energetic Mater* 4:273-303 (1986)).

There are several compounds of interest other than those belonging to the EPA Method 8330 suite of fourteen that can be determined on the existing system. These include nitroguanidine, picric acid, ethylene glycol dinitrate (EGDN), nitroglycerin, and pentaerythritol tetranitrate (PETN). These compounds are typically separated on a reversed-phase HPLC system and detected by UV at low wavelengths. UV detection at 254 nm and 220 nm were compared to PAED, and the limits of detection are listed in table 1. In all cases, PAED proved to be much more sensitive than UV at 254 nm and 220 nm for each of the five compounds. Furthermore, EGDN and PETN cannot be detected in trace amounts by EPA Method 8330, but they can be easily determined by PAED. All five of these compounds were satisfactorily resolved from the EPA Method 8330 compounds, as seen in the PAED chromatogram in FIG. 4. Furthermore, using the existing system, one ground water sample can be monitored for nineteen explosives in a single chromatographic run (additional explosives include nitroguanidine, EGDN, pictic acid, nitroglycerin and PETN), and this is not addressed in EPA Method 8330.

On-Line SPE

When a real ground water sample was injected into the analysis system through the 100 μL injection loop, a large background appeared on the electrochemical detector that completely overwhelmed any signal from the explosive residues, causing negative peaks, as seen in FIG. 5. It was evident that sample clean up was needed prior to injection on the HPLC. The advantage of on-line SPE is shown in FIG. 6. The small shift in retention time is due to retention on the small column. The high background is virtually eliminated, and the S/N ratio is improved tremendously.

Analytical figures of merit were determined for explosive residues in deionized water using on-line SPE, and they are listed in table 3B. In general, limits of detection and quantitation were decreased by about an order of magnitude over the direct injection method, while linearity and low relative standard deviations were maintained. Of significance is the sensitivity achieved for the nitramines, HMX and RDx, two compounds of great environmental consequence. These compounds do not respond as well as the other compounds under the EPA 8330 Method, but they respond the best with PAED with detection limits in the low to sub-parts-per-trillion level. TNT, another common contaminant, is also very sensitive to PAED, having a detection limit of almost an order of magnitude lower than that of Method 8330. With on-line SPE, limits of detection are superior to those achieved using EPA Method 8330, and only 2 mL of sample is required as opposed to an entire liter required by EPA Method 8330.

TABLE 3B

Analytical figures of merit by on-line SPE.

| Explosive | Detection | LOD[a] (ug/L) | m | b | $R^2$ | LOQ[b] (ug/L) | % RSD n = 7 |
|---|---|---|---|---|---|---|---|
| 1 | UV | 0.04 | 2375046 | 3611 | 0.99931 | 0.6 |  |
|   | PAED | 0.0007 | 530804816 | 32445 | 0.99987 | 0.01 | 5.38 |
| 2 | UV | 0.1 | 3688869 | 1922 | 0.99919 | 2 |  |
|   | PAED | 0.002 | 511876487 | 74400 | 0.99922 | 0.03 | 3.16 |
| 3 | UV | 0.07 | 7587023 | 58 | 0.99917 | 1 |  |
|   | PAED | 0.008 | 120733258 | −11449 | 0.99948 | 0.1 |  |
| 4 | UV | 0.06 | 10817046 | 1632 | 0.99955 | 1 |  |
|   | PAED | 0.03 | 33333127 | 11235 | 0.99974 | 0.5 |  |

TABLE 3B-continued

Analytical figures of merit by on-line SPE.

| Explosive | Detection | LOD$^a$ (ug/L) | m | b | $R^2$ | LOQ$^b$ (ug/L) | % RSD n = 7 |
|---|---|---|---|---|---|---|---|
| 5 | UV | 0.05 | 6572014 | 569 | 0.99971 | 2 | |
|   | PAED | 0.04 | 35730659 | −15748 | 0.99957 | 0.9 | |
| 6 | UV | 0.2 | 5181264 | 804 | 0.99982 | 3 | |
|   | PAED | 0.007 | 146103947 | 66998 | 0.99950 | 0.1 | |
| 7 | UV | 0.09 | 7408222 | 2870 | 0.99917 | 2 | |
|   | PAED | 0.02 | 63700692 | 2833 | 0.99973 | 0.3 | 2.64 |
| 8 | UV | 0.08 | 5147257 | 1078 | 0.99990 | 0.3 | |
|   | PAED | 0.1 | 16781705 | −118 | 0.99992 | 0.4 | |
| 9 | UV | 0.05 | 5145178 | 3289 | 0.99995 | 0.17 | |
|   | PAED | 0.05 | 25886203 | 10101 | 0.99991 | 0.17 | |
| 10 | UV | 0.04 | 8107759 | 4710 | 0.99994 | 0.15 | |
|    | PAED | 0.2 | 12842597 | 3849 | 0.99990 | 0.5 | |
| 11 | UV | 0.04 | 10441174 | 1917 | 0.99998 | 0.14 | |
|    | PAED | 0.09 | 27704511 | 7444 | 0.99996 | 0.3 | |
| 12 | UV | 0.3 | 3987859 | −940 | 0.99974 | 5 | |
|    | PAED | 0.1 | 26831251 | −7335 | 0.99941 | 2 | |
| 13 | UV | 0.4 | 3566579 | −1080 | 0.99987 | 7 | |
|    | PAED | 0.2 | 13729809 | −8603 | 0.99919 | 3 | |
| 14 | UV | 0.4 | 4526009 | −1550 | 0.99987 | 5 | |
|    | PAED | 0.4 | 8779970 | −1160 | 0.99874 | 6 | |

Validation

Because this system will be used for environmental fieldwork, it has been validated using standards set forth by the Resource Conservation and Recovery Act (RCRA), enacted by Congress in 1976. RCRA requires an evaluation of the method with respect to accuracy (80-120%), precision (<20%), repeatability (<15%), and quantitation and detection limits in the matrix of interest. Analytical figures of merit for explosive residues spiked into ground water are listed in table 4. Both detectors retain good linearity, and both precision and accuracy fall within RCRA guidelines. Although some sensitivity is lost due to matrix effects, the limits of detection in ground water with SPE are lower than those achieved with the direct injection method.

TABLE 4

Analytical figures of merit for explosive residues spiked into blank ground water.

| Explosive | Detection | LOD$^a$ (ug/L) | m | b | $R^2$ | LOQ$^b$ (ug/L) | % RSD n = 7 |
|---|---|---|---|---|---|---|---|
| 1 | UV | 0.2 | 3727396 | 1736 | 0.99939 | 0.7 | |
|   | PAED | 0.004 | 335572515 | 93978 | 0.99982 | 0.01 | 13% |
| 2 | UV | 0.6 | 3934298 | −1824 | 0.99998 | 2 | |
|   | PAED | 0.006 | 402950611 | −153648 | 0.99821 | 0.02 | 8% |
| 3 | UV | 0.3 | 7039598 | −4032 | 0.99932 | 1 | |
|   | PAED | 0.05 | 100549387 | −48786 | 0.99860 | 0.1 | |
| 4 | UV | 0.1 | 9598515 | 25124 | 0.99831 | 0.2 | |
|   | PAED | 0.07 | 38545526 | 38057 | 0.99831 | 0.2 | |
| 5 | UV | 0.2 | 6673138 | −153 | 0.99778 | 0.6 | |
|   | PAED | 0.02 | 30686076 | −1952 | 0.99925 | 0.2 | |
| 6 | UV | 0.1 | 10357198 | 5106 | 0.99606 | 0.3 | |
|   | PAED | 0.02 | 160833997 | −58796 | 0.99879 | 0.07 | |
| 7 | UV | 0.2 | 7546564 | 521 | 0.99908 | 0.6 | |
|   | PAED | 0.06 | 61342625 | −22311 | 0.99865 | 0.1 | 5% |
| 8 | UV | 0.2 | 2740651 | −1256 | 0.99999 | 0.7 | |
|   | PAED | 0.5 | 8931537 | −871 | 1.00000 | 1.7 | |
| 9 | UV | 0.1 | 2450297 | 2714 | 0.99999 | 0.4 | |
|   | PAED | 0.3 | 11801884 | −6877 | 0.99995 | 1.2 | |
| 10 | UV | 0.07 | 8054742 | 5699 | 0.99997 | 0.2 | |
|    | PAED | 0.9 | 3688344 | −181 | 0.99994 | 4 | |
| 11 | UV | 0.08 | 4921502 | 6218 | 0.99998 | 0.3 | |
|    | PAED | 0.4 | 12491873 | −8692 | 0.99993 | 1.2 | |
| 12 | UV | 1 | 4268597 | −2284 | 0.99816 | 3 | |
|    | PAED | 0.08 | 21849583 | 2454 | 0.99874 | 0.3 | |
| 13 | UV | 2 | 3716345 | −2830 | 0.99732 | 4 | |
|    | PAED | 0.2 | 12709611 | 1086 | 0.99919 | 0.8 | |
| 14 | UV | 2 | 4584982 | −3187 | 0.99969 | 7 | |
|    | PAED | 0.2 | 10152957 | −11917 | 0.99191 | 5 | |

For further validation, a series of blind samples were made and run on the system. The samples were run by direct injection and on-line SPE. The results are reported in table 5. Percent recoveries ranged from 89 to 110%, all within those accepted by RCRA. No further samples were investigated, as it was not required by RCRA. The method has proven to be successful in determining explosive residues in ground water with on-line SPE.

and the results are listed in table 6. The table reports the amount of explosive residue contained in the sample (target value), the acceptable range of quantitation, the results found by direct injection and SPE (by PAED and UV detection), the standard deviation based on six injections (stdev), and the percent recovery. All recoveries of explosive residues fell

TABLE 5

Results of Blind Studies.

| Samples in D.I. Water | Explosive | Spiked Amount (ug/mL) | Determined Amount, UV | Determined Amount, PAED | % Recovery UV | % Recovery PAED |
|---|---|---|---|---|---|---|
| 1 | TNT | 14.9 | 13.8 ± 1.8 | 14.7 ± 0.7 | 93 | 99 |
| 2 | TNT | 21.9 | 20.3 ± 1.9 | 19.4 ± 0.6 | 93 | 89 |
| 3 | TNT | 40.0 | 39.0 ± 2.5 | 37.0 ± 0.4 | 98 | 93 |
| 4 | TNT | 35.0 | 38.0 ± 4.0 | 34.0 ± 8.0 | 108 | 97 |

| Samples in Ground Water | Explosive | Spiked Amount (ug/mL) | Determined Amount, UV | Determined Amount, hv-EC | % Recovery UV | % Recovery hv-EC |
|---|---|---|---|---|---|---|
| 5 | TNT | 10.0 | 9.0 ± 0.7 | 11.0 ± 0.7 | 90 | 110 |

For the final phase of validation for ground water samples, a certified sample was purchased from Environmental Resource Associates, Arvada, Colo. The sample was analyzed by both the direct injection method and by on-line SPE, within ranges accepted by RCRA. An important note is that values obtained from the UV and PAED detectors agree with each other, and that the direct injection method agrees with the on-line SPE method.

TABLE 6

Certified sample results by direct injection and SPE.

| Explosive | Target Value (ug/L) | Accepted Range | Direct Injection UV | Direct Injection PAED | % Recovery UV | % Recovery PAED | SPE UV | SPE PAED | % Recovery UV | % Recovery PAED |
|---|---|---|---|---|---|---|---|---|---|---|
| 1 | 15.20 | 8.44-19.8 | 15.21 | 15.28 | 100.1 | 100.5 | 15.08 | 15.14 | 99.2 | 99.6 |
| Stdev (n = 6) | | | 0.31 | 0.06 | | | 0.45 | 0.19 | | |
| 2 | 9.20 | 6.71-11.40 | 8.84 | 8.93 | 96.0 | 97.0 | 8.79 | 8.76 | 95.5 | 95.3 |
| Stdev (n = 6) | | | 0.17 | 0.26 | | | 0.09 | 0.05 | | |
| 3 | 7.00 | 4.51-7.42 | 7.30 | 7.29 | 104.3 | 104.1 | 7.35 | 7.28 | 104.9 | 104.1 |
| Stdev (n = 6) | | | 0.05 | 0.25 | | | 0.26 | 0.04 | | |
| 4 | 10.40 | 8.17-11.50 | 10.08 | 9.98 | 96.9 | 95.9 | 10.11 | 10.11 | 97.2 | 97.2 |
| Stdev (n = 6) | | | 0.07 | 0.11 | | | 0.05 | 0.06 | | |
| 5 | 10.00 | 6.29-13.80 | 9.39 | 9.40 | 93.9 | 94.0 | 10.09 | 10.05 | 100.9 | 100.5 |
| Stdev (n = 6) | | | 0.10 | 0.17 | | | 0.07 | 0.23 | | |
| 6 | 15.70 | 9.45-19.80 | 15.18 | 15.24 | 96.7 | 97.1 | 15.22 | 15.15 | 96.9 | 96.5 |
| Stdev (n = 6) | | | 0.13 | 0.34 | | | 0.14 | 0.06 | | |
| 7 | 9.82 | 7.04-12.70 | 9.43 | 9.43 | 96.0 | 96.1 | 9.45 | 9.45 | 96.3 | 96.2 |
| Stdev (n = 6) | | | 0.16 | 0.12 | | | 0.05 | 0.07 | | |
| 8 | 8.20 | 5.22-9.68 | 8.30 | 8.31 | 101.2 | 101.3 | 8.41 | 8.44 | 102.6 | 103.0 |
| Stdev (n = 6) | | | 0.09 | 0.11 | | | 0.02 | 0.11 | | |
| 9[c] | 9.42 | 6.62-10.70 | 7.25 ± 0.36 | | 77.0 | | | | | |
| Stdev (n = 6) | | | | | | | | | | |
| 10[c] | 6.21 | 4.99-7.08 | 6.28 ± 0.38 | | 101.1 | | | | | |
| Stdev (n = 6) | | | | | | | | | | |
| 11 | 5.62 | 4.69-6.13 | 5.58 | 5.68 | 99.2 | 101.1 | 5.63 | 5.77 | 100.2 | 102.6 |
| Stdev (n = 6) | | | 0.21 | 0.12 | | | 0.06 | 0.23 | | |
| 12 | 16.80 | 12.70-17.80 | 17.09 | 17.05 | 101.7 | 101.5 | 17.26 | 17.20 | 102.7 | 102.4 |
| Stdev (n = 6) | | | 0.44 | 0.40 | | | 0.33 | 0.34 | | |
| 13 | 6.21 | 4.26-6.52 | 6.54 | 6.51 | 105.2 | 104.8 | 6.25 | 6.27 | 100.7 | 100.9 |
| Stdev (n = 6) | | | 0.34 | 0.50 | | | 0.03 | 0.04 | | |
| 14 | 7.40 | 6.13-7.62 | 6.90 | 7.01 | 93.2 | 94.7 | 7.01 | 6.86 | 94.7 | 92.7 |
| Stdev (n = 6) | | | 0.33 | 0.34 | | | 0.08 | 0.30 | | |

[c]Determined chemometrically.

Extraction from Soil Samples

The instrument used for pressurized fluid extraction (PFE) is the Accelerated Solvent Extractor 200 (ASE 200, Dionex). The solvent is 100% methanol, HPLC Grade (Fisher, Pittsburgh, Pa.).

Two certified soil samples were purchased from Environmental Resource Associates in order to evaluate the applicability of PFE to soil samples and to test the HPLC system for determining explosive residues in soil extracts. PFE using ASE technology (see B. E. Richter et al.) was used to extract the first soil sample. The extract was contained in 100% methanol, and it was diluted 1:10 in deionized water and directly injected through a syringe filter into the HPLC-UV-PAED system. Typical chromatograms of a soil sample are shown in FIG. 7 and FIG. 8. This extraction was performed prior to optimization of PFE parameters. The compounds of interest are easily identified on the PAED chromatogram (FIG. 8), while lack of sensitivity and interfering peaks make it more difficult on the UV chromatogram (FIG. 7). However, when extracting the first certified soil sample, it was determined that recoveries for some explosive residues were rather poor for this PFE method (about 50%), so several parameters needed to be further optimized on the ASE. This soil sample was extracted under varying conditions to determine optimum extraction parameters.

The most important parameter to be varied was temperature (B. E. Richter, et al., *Anal. Chem.* 68:1033-1039 (1996)) and each extract of the first certified soil sample, contained in 100% methanol, was diluted 1:10 in deionized water and directly injected on the HPLC-UV-PAED system for evaluation. The temperatures used were 100° C., 125° C., 150° C., and 175° C. and the other parameters, 1500 psi pressure, a static time of 10 minutes, two static cycles, a flush volume of 60%, and a purge time of 200 seconds, were held constant. It was determined that a temperature of 150° C. yielded the best recoveries. Increasing the pressure and the number of static cycles showed no improvement. Acetone, which is also suggested for use by the Dionex: method, was substituted for methanol under the above conditions, but methanol gave the best recoveries. The results of the certified soil sample using the optimized PFE method are shown in table 7. Although the recoveries are not 100%, they are within the performance acceptance limits, showing that this ASE method is acceptable for extracting explosive residues from soil.

TABLE 7

Results of Certified Soil Sample.

| Explosive | Target Value (ug/kg) | Performance Acceptance Limits | Amount Found, UV | Amount Found, PAED |
|---|---|---|---|---|
| NB | 12400 | 7730-15100 | 8990 ± 170 | 9340 ± 350 |
| % Recovery | | | 72 | 75 |
| 2,6-DNT | 3540 | 2160-4570 | 2260 ± 2 | 2250 ± 32 |
| % Recovery | | | 64 | 64 |
| 2-NT | 7500 | 5390-9230 | 5970 ± 143 | 6130 ± 178 |
| % Recovery | | | 80 | 82 |
| 4-NT | 13000 | 10300-14100 | 11550 ± 283 | 11630 ± 458 |
| % Recovery | | | 89 | 89 |
| 3-NT | 4100 | 3400-4380 | 3480 ± 153 | 3450 ± 218 |
| % Recovery | | | 85 | 84 |

Comparison of Extraction Techniques.

Jenkins and Grant reported that sonication in acetonitrile is the best overall choice for extracting explosive residues from soil (T. F. Jenkins and C. L. Grant, *Anal. Chem.* 59:1326-1331 (1987)), and this method was adopted by EPA Method 8330. Therefore, this sonication method was compared to ASE extraction using the HPLC-UV-PAED system. The second soil sample purchased from Environmental Resource Associates was used for this experiment.

As seen in table 8, sonication of soil resulted in approximately 50% more recovery than extraction with the optimized ASE method for all explosive residues except for 4-amino-2,6-dinitrotoluene, whose recoveries were very similar using either method. It is important to point out here, however, that results obtained between UV and PAED with either extraction method agree with one another, and no matter which extraction method is used, HPLC-UV-PAED is a good method for determining explosive residues in soil extracts. It should be further noted that because PAED is so sensitive, one may not need 100% recovery to determine whether or not a site is contaminated with explosive residues. Also, PFE is fast, allowing for approximately thirty-minute extractions rather than eighteen-hour extractions, amenable to doing on-site analyses.

TABLE 8

Comparison of Extraction Techniques Using HPLC-UV-PAED

| | Sonication | | PFE | |
|---|---|---|---|---|
| Explosive | Amount Found (ug/kg) UV | Amount Found, (ug/kg) PAED | Amount Found (ug/kg) UV | Amount Found, (ug/kg) PAED |
| HMX | 5700 ± 32 | 5640 ± 43 | 2690 ± 28 | 2770 ± 47 |
| RDX | 8430 ± 56 | 8390 ± 33 | 4210 ± 1 | 3830 ± 55 |
| TNB | 17500 ± 97 | 17060 ± 104 | 8880 ± 48 | 8870 ± 42 |
| DNB | 12400 ± 75 | 12200 ± 154 | 6620 ± 51 | 6720 ± 69 |
| NB | 19300 ± 374 | 19376 ± 120 | 10840 ± 276 | 10970 ± 174 |
| TNT | 6630 ± 11 | 6550 ± 76 | 4020 ± 11 | 4130 ± 36 |
| 4-A-2,6-DNT | 1860 ± 14 | 1880 ± 32 | 1770 ± 9 | 1790 ± 42 |

CONCLUSIONS

HPLC-UV-PAED with on-line SPE is a proven method for the determination of explosive residues. Enhanced sensitivity and selectivity means that less sample and sample preparation are required. Also, this approach is compatible with on-site analysis of ground water and soil analyses, allowing fast assessment and profiling of contaminated sites.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for sampling one or more analytes of a soil sample, comprising:
   (a) extracting the one or more analytes from the soil sample to generate a liquid sample;
   (b) passing the liquid sample through one or more pre-concentration chromatographic columns, thereby retaining said one or more analytes on the one or more pre-concentration chromatographic columns and concentrating said one or more analytes;
   (c) delivering a solvent to the one or more pre-concentration chromatographic columns, thereby eluting said one or more analytes from the one or more pre-concentration chromatographic columns to give an eluate;
   (d) passing the eluate through one or more analytical chromatographic columns, thereby separating said one or more analytes; and
   (e) analyzing the separated one or more analytes in a variable wavelength detector and then a photo-assisted electrochemical detector, wherein the two detectors function in-line together, and wherein the lower limit of detection of the one or more analytes achieved electrochemically is about 10 to about 1000 times less than those achieved by the variable wavelength detector.

2. The method of claim 1, wherein said one or more analytes is selected from the group consisting of nitroso compounds, organic nitro compounds, organothiophosphates, PAHs and drug metabolites.

3. The method of claim 1, further comprising holding the liquid sample in a sample loop prior to (b).

4. The method of claim 3, further comprising drawing the liquid sample from a liquid reservoir into the sample loop.

5. The method of claim 1, further comprising washing the one or more analytes on the one or more pre-concentration chromatographic columns prior to (c).

6. The method of claim 5, wherein said washing comprises washing with methanol in a solution of acetate and sodium chloride.

7. The method of claim 6, wherein said washing comprises washing with 7.5% methanol in 20 mM acetate and 0.5 M sodium chloride.

8. The method of claim 1, wherein said delivering in (c) comprises backflushing the solvent through the one or more pre-concentration chromatographic columns, thereby resulting in fractionation and concentration of the one or more analytes.

9. The method of claim 8, wherein the solvent comprises methanol and acetate.

10. The method of claim 9, wherein the solvent comprises 50% methanol in 20 mM acetate buffer at pH 4.5.

11. The method of claim 1, wherein said method is used to sample the soil sample on-site.

12. A method for on-site sampling of one or more explosive residues of a soil sample, comprising:
   (a) extracting the one or more explosive residues from the soil sample to generate a liquid sample;
   (b) drawing the liquid sample from an on-site liquid reservoir into a sample loop and holding the liquid sample in the sample loop;
   (c) passing the liquid sample from the sample loop through one or more pre-concentration chromatographic columns, thereby retaining said one or more explosive residues on the one or more pre-concentration chromatographic columns and concentrating said one or more explosive residues;
   (d) delivering a solvent to the one or more pre-concentration chromatographic columns, thereby eluting said one or more explosive residues from the one or more pre-concentration chromatographic columns to give an eluate;
   (e) passing the eluate through one or more high-performance liquid chromatography columns, thereby separating the one or more explosive residues on the one or more high-performance liquid chromatography columns; and
   (f) analyzing the separated one or more explosive residues in a variable wavelength detector and then in a photo-assisted electrochemical detector, wherein the lower limit of detection of the one or more explosive residues achieved electrochemically is about 10 to about 1000 times less than those achieved by the variable wavelength detector.

13. The method of claim 12, further comprising washing the one or more explosive residues on the one or more pre-concentration chromatographic columns prior to (d).

14. The method of claim 13, wherein said washing comprises washing with methanol in a solution of acetate and sodium chloride.

15. The method of claim 14, wherein said washing comprises washing with 7.5% methanol 20 mM acetate and 0.5 M sodium chloride.

16. The method of claim 12, wherein said delivering in (d) comprises backflushing the solvent through the one or more pre-concentration chromatographic columns, thereby resulting in partial fractionation and concentration of the one or more explosive residues.

17. The method of claim 16, wherein the solvent comprises methanol and acetate.

18. The method of claim 17, wherein the solvent comprises 50% methanol in 20 mM acetate buffer at pH 4.5.

* * * * *